(12) United States Patent
Hoffmann et al.

(10) Patent No.: US 6,242,392 B1
(45) Date of Patent: Jun. 5, 2001

(54) GRINDING AIDS FOR X-RAY FLUORESCENCE ANALYSIS

(75) Inventors: Frank Hoffmann, Darmstadt; Wolfgang Martens, Ober-Ramstadt; Manfred Wachsmann, Höchst, all of (DE)

(73) Assignee: Merck Patent Gesellschaft mit (DE)

( * ) Notice: Subject to any disclaimer, the term of this patent is extended or adjusted under 35 U.S.C. 154(b) by 0 days.

(21) Appl. No.: 09/386,964

(22) Filed: Aug. 31, 1999

(30) Foreign Application Priority Data

May 11, 1999 (DE) .............................. 199 21 549

(51) Int. Cl.⁷ ..................... G01N 23/223; C10M 141/00
(52) U.S. Cl. ................. 508/220; 508/216; 508/459; 378/45
(58) Field of Search ................................ 508/459, 216, 508/220; 378/45

(56) References Cited

U.S. PATENT DOCUMENTS

| 3,830,437 | * | 8/1974 | Everett | 241/137 |
| 4,919,342 | * | 4/1990 | Narukawa | 241/25 |
| 5,161,409 | * | 11/1992 | Hughes et al. | 73/153 |
| 5,257,302 | * | 10/1993 | Narukawa | 378/45 |

FOREIGN PATENT DOCUMENTS

| 690302 | * | 1/1996 | (EP) . |
| 1561017 | * | 4/1990 | (SU) . |

* cited by examiner

*Primary Examiner*—Jacqueline V. Howard
(74) *Attorney, Agent, or Firm*—Millen, White, Zelano & Branigan, P.C.

(57) ABSTRACT

The invention relates to grinding aids for X-ray fluorescence analysis which consist of a polysaccharide binder, sugar or sugar alcohols as filler and of a lubricant. The grinding aids according to the invention are easy to use and provide very reproducible analytical data.

7 Claims, No Drawings

GRINDING AIDS FOR X-RAY FLUORESCENCE ANALYSIS

The invention relates to grinding aids for X-ray fluorescence analysis (XRF).

Sample preparation is very important in XRF. Correct analytical results can be obtained only with careful sample preparation. Metallic samples ought to be finely machined on one side, and possibly ground or polished. Organic and biological samples can be ashed. Oxide samples such as rocks, glasses, slags etc. can be powdered, ground to a uniform fineness and possibly compressed with a grinding aid or binder.

Determination of low concentrations of uranium, thorium and potassium via XRF is described in Chemical Geology 38, page 225, 1983. This entails adding a few drops of polyvinylpyrrolidone/methylcellulose binder to a finely ground, homogenized rock powder, and compressing in the form of tablets and analysing.

EP 0690302 describes a grinding aid composed of polyvinylpyrrolidone and microcrystalline cellulose.

In addition, tablets of Canada balsam and cellulose provided with a sugar coating are commercially available for sample preparation. These tablets are finely ground by the user together with the sample to be investigated, and compressed anew in the form of tablets with which the XRF is then carried out.

All known aids have considerable disadvantages. Tablets of polyvinylpyrrolidone and methylcellulose are not stable to fracture. Air conditioning is necessary for usage of the grinding aids composed of polyvinylpyrrolidone and microcrystalline cellulose because they are hygroscopic. Canada balsam in turn is tacky and therefore can be homogenized with cellulose and processed only with difficulty. In addition, the tablets must be sugar-coated in order to avoid adhesion during storage. This makes an additional production step necessary.

It is therefore an object of the present invention to provide grinding aids for XRF which do not have the disadvantages mentioned and whose production and usage are as simple as possible.

It has been found that grinding aids composed of binders such as cellulose, fillers such as lactose, and lubricants such as stearic acid have ideal properties for sample preparation for XRF. Grinding aids of this composition can be processed easily, are not tacky and are not hygroscopic.

The invention therefore relates to grinding aids which consist of a filler (2 to 50% by weight), of a lubricant (0 to 3% by weight) and of a binder (47 to 98% by weight).

A preferred embodiment comprises grinding aids consisting of lactose, stearic acid and microcrystalline cellulose.

A preferred embodiment comprises grinding aids in the form of powders or tablets.

The invention further relates to the use of a grinding aid according to the invention for sample preparation for X-ray fluorescence analysis.

The compositions according to the invention are ground with the sample in accordance with the usage of known compositions and are compressed to the final tablets which are then measured by XRF. General information on usage is to be found in K. H. Koch, K. D. Ohls, J. Flock, Steel Technology International, pages 293–298, Sterling Publications International, London, 1990 or K. H. Koch, K. D. Ohls, J. Flock, Rationalisierung der Multi-Elementanalytik durch Einsatz der RFA [Rationalization of Multielement Analysis by Use of XRF], Laborpraxis 14, pages 1022–1027, 1990.

In general, the dosage of the composition according to the invention does not differ from the dosage of conventional compositions. Typically, about 2 g of the grinding aid are added to 20 g of a sample.

Grinding aids ought, besides simple production and usage, to meet the following requirements:

Elevated temperatures during the grinding lead to increased adhesion of the mixture of grinding aid and sample in the grinding vessel. Accordingly, the temperature during the grinding should be kept as low as possible by the grinding aids so that the samples can be processed more rapidly in succession, since the grinding vessel does not need so long to cool.

To minimize particle size effects on the analysis, very fine grinding is necessary. The samples should therefore be ground very fine in the shortest possible time (evolution of heat).

After the grinding, it should be possible to remove the mixture of sample and grinding aid from the grinding vessel without residues. Hence grinding aids should prevent adhesion of the mixture of grinding aid and sample to the walls of the grinding vessel (scale formation).

The final tablet must have a certain minimum hardness in order not to be damaged during transfer from the press to the XRF and during the measurement.

The abovementioned requirements are taken into account by the individual components of the composition according to the invention. The compositions according to the invention for XRF preferably consist of a polysaccharide binder, of a sugar or sugar alcohol as filler and of a lubricant.

Binders which can be used for the grinding aid according to the invention are polysaccharides and polysaccharide derivatives, in particular starch (for example maize, rice, potato or wheat starch), modified starches (for example cold-soluble starch, hydroxy-ethylstarch), cellulose (cellulose powder, microcrystalline cellulose) or cellulose derivatives (methylcellulose, carboxymethylcellulose), particularly preferably microcrystalline cellulose.

Fillers used according to the invention are sugars or sugar alcohols, in particular lactose, mannitol, glucose or sucrose, particularly preferably lactose.

Lubricants are, according to the invention, in particular stearic acid, palmitic acid, stearyl, cetyl or myristyl alcohol, glycerol fatty acid esters (for example esters or mixed esters of palmitic or stearic acid with glycerol), polyethylene glycols or paraffin, particularly preferably stearic acid. Calcium hydrogen phosphate or salts of the abovementioned acids cannot be used as lubricants for grinding aids for XRF because they would falsify the result of the XRF.

The percentage composition of the components depends on the exact use, in particular the characteristics of the sample. The grinding aids according to the invention preferably comprise between 0 and 3% by weight of lubricant, particularly preferably between 1 and 2.5% by weight. The lubricant prevents scale formation in the grinding vessel at high speeds of rotation, so that fewer residues remain in the grinding vessel. On the other hand, the addition of lubricants influences the characteristics of the final tablet. The final tablet will be too soft if too much lubricant is added. For this reason, the content of lubricant in the grinding aid according to the invention must be carefully metered. With hard samples, contents of about 2% by weight result in final tablets of good quality. If, on the other hand, the samples are soft, a content of 0.5% by weight or less of lubricant may suffice. The skilled person aware of the differences in characteristics of the sample material is able suitably to vary the content of lubricant in the grinding aid according to the invention. Grinding aids according to the invention which comprise lubricants are also particularly suitable for soft samples when they are added in tablet form.

The filler content of the composition according to the invention is preferably between 2 and 50% by weight, particularly preferably between 5 and 20% by weight. As the content of filler increases it is often no longer possible to ensure tabletability of the final tablet. However, in some cases, it is also possible to use compositions with filler contents above 50% by weight; however, it is then necessary to add more grinding aid than usual to the sample, so that the detection limit of the analysis deteriorates.

The content of binder is adapted according to the two other components. With a preferred filler content of 5 to 20% by weight a content of up to 3% by weight of lubricant, the content of binder is typically 77 to 95% by weight.

Grinding aids composed of microcrystalline cellulose, lactose monohydrate and stearic acid have proved to be particularly preferred for many applications. The lactose content in this case is between 5 and 20% by weight, preferably 10% by weight, the stearic acid content is between 0 and 2.5% by weight, preferably 2% by weight, and the content of cellulose is between 77.5 and 95% by weight, preferably 88% by weight.

The grinding aids according to the invention can be used as granules, compacts, preferably as powders or, particularly preferably, as tablet. The tablets can be produced in various sizes so that dosage according to the sample size is possible.

The grinding aids according to the invention thus represent a considerable improvement by comparison with compositions previously disclosed. Since the substances they contain are neither tacky nor very hygroscopic, they are distinguished by simplicity of usage and production. In tableted form in particular they have unlimited suitability for fully automatic processes. Measurements on various samples such as, for example, from the steel and cement industry sectors have led to reproducible results.

Even without further statements, it is assumed that a skilled person will be able to utilize the above description. The preferred embodiments and examples are therefore to be regarded merely as a descriptive, and certainly not in any way limiting, disclosure.

The complete disclosure of all the applications, patents and publications mentioned hereinbefore and hereinafter is incorporated in this application by reference.

EXAMPLE

The grinding aids according to the invention are compared in terms of their properties with grinding aid tablets based on Canada balsam and available on the market.

The materials used for the tests were sinter and blast furnace slag. The amount of sample per grinding step was always 20 g plus 2 g of grinding aid.

To measure the temperature, a thermosensor was inserted immediately after opening the grinding vessel. The residues adhering in the grinding vessel were determined by reweighing the ground sample material. The particle size was determined using a laser diffraction particle analyser. The hardness of the final tablets was determined using a manual lever-type tester.

The grinding aid according to the invention was used in the following composition: 88% by weight cellulose, 10% by weight lactose, 2% by weight stearic acid.

The analytical data for the sample materials had previously been determined by wet-chemical methods (data in % by weight):

Sinter Material

| $SiO_2$ | $Al_2O_3$ | CaO | P | MgO | $Fe_{tot}$ | $TiO_2$ | Mn | Cr |
|---|---|---|---|---|---|---|---|---|
| 4.97 | 1.10 | 9.33 | 0.039 | 0.98 | 57.81 | 0.091 | 0.25 | 0.02 |

Blast Furnace Slag

| $SiO_2$ | $Al_2O_3$ | CaO | P | MgO | $Fe_{tot}$ | $TiO_2$ | Mn |
|---|---|---|---|---|---|---|---|
| 34.8 | 10.9 | 41.6 | 0.0022 | 7.21 | 0.43 | 2.6 | 0.17 |

Comparison in Terms of Grinding Temperature, Residues, Hardness and Grinding Fineness Grinding Temperature The temperature rise ($\Delta T$ [°C.]) during a grinding was determined relative to the temperature rise on use of the commercially available grinding aid. Thus, negative $\Delta T$ values mean that the temperature rise is less than on use of the commercially available grinding aid.

| | $\Delta T$ sinter | $\Delta T$ blast furnace slag |
|---|---|---|
| Composition according to the invention | −5 | −2 |

Residues

| | Sinter Residue [g] | Blast furnace slag Residue [g] |
|---|---|---|
| Composition according to the invention | 0.5 | <0.5 |
| Conventional composition | 3–4 | 4–5 |

Hardness

|  | Sinter Hardness [N/mm²] | Blast furnace slag Hardness [N/mm²] |
| --- | --- | --- |
| Composition according to the invention | 180 | 170 |
| Conventional composition | 180 | 150 |

Grinding Fineness

The parameter used was D(v, 0.9), that is to say the diameter in µm below which 90% of the diameters of the measured particles lie.

|  | Sinter D(v, 0.9) | Blast furnace slag D(v, 0.9) |
| --- | --- | --- |
| Composition according to the invention | 19 | 24 |
| Conventional composition | 19 | 23 |

These results show that the temperature during the grinding remains significantly lower than on use of conventional grinding aids. This makes it possible to shorten the analysis cycle time. Because of the small residues in the grinding vessel, the cleaning effort after grinding is less and the risk of carryovers is reduced.

The entire disclosure of corresponding German application No. DE 199 21 549.9 filed May 11, 1999 is hereby incorporated by reference.

The preceding examples can be repeated with similar success by substituting the generically or specifically described reactants and/or operating conditions of this invention for those used in the preceding examples.

What is claimed is:

1. Grinding aid consisting essentially of 47 to 98% by weight of a binder, 2 to 50% by weight of a filler and 0 to 3% by weight of a lubricant wherein the binder comprises one or more polysaccharides polysaccharide derivatives or both and the filler comprises one or more sugars, sugar alcohols or both.

2. Grinding aid consisting essentially of 47 to 98% by weight of a binder, 2 to 50% by weight of a filler and 0 to 3% by weight of a lubricant, which comprises microcrystalline cellulose as binder, lactose as filler and stearic acid as lubricant.

3. Grinding aid according to claim 1 which is in the form of a powder.

4. Grinding aid according to claim 1 which is in the form of tablets.

5. Grinding aid according to claim 2 which is in the form of a powder.

6. Grinding aid according to claim 2 which is in the form of tablets.

7. A method of using a grinding aid according to claim 1 which comprises preparing a sample preparation for X-ray fluorescence analysis with said grinding aid.

* * * * *